United States Patent [19]

Pitts, Jr. et al.

[11] 4,282,760

[45] Aug. 11, 1981

[54] MULTIPHASE FLUID FLOW METER (D#76,244)

[75] Inventors: Robert W. Pitts, Jr.; Dan M. Arnold; Hans J. Paap, all of Houston, Tex.

[73] Assignee: Texaco Inc., White Plains, N.Y.

[21] Appl. No.: 114,482

[22] Filed: Jan. 23, 1980

[51] Int. Cl.³ .............................................. G01F 1/88
[52] U.S. Cl. ............................ 73/861.02; 73/861.04; 73/861.69
[58] Field of Search .......... 73/861.01, 861.02, 861.04, 73/861.35, 861.69

[56] References Cited

U.S. PATENT DOCUMENTS 4,144,754   3/1979   Pitts et al. ........................ 73/861.02

FOREIGN PATENT DOCUMENTS 281845   6/1971   U.S.S.R. ................................. 73/861.69

Primary Examiner—James J. Gill
Attorney, Agent, or Firm—Carl G. Ries; Robert A. Kulason; Henry C. Dearborn

[57] ABSTRACT

An improved multiphase fluid flow meter for fluid which contains gas. It has a full circle loop to subject the flowing fluid to centrifugal force, and it can measure the pressure differentials between the center and the outside and inside radii of the loop. Also it can measure the density of the average fluid flowing, plus the density of a continuous sampling of the gas and of the liquid constituent of the fluid.

8 Claims, 7 Drawing Figures

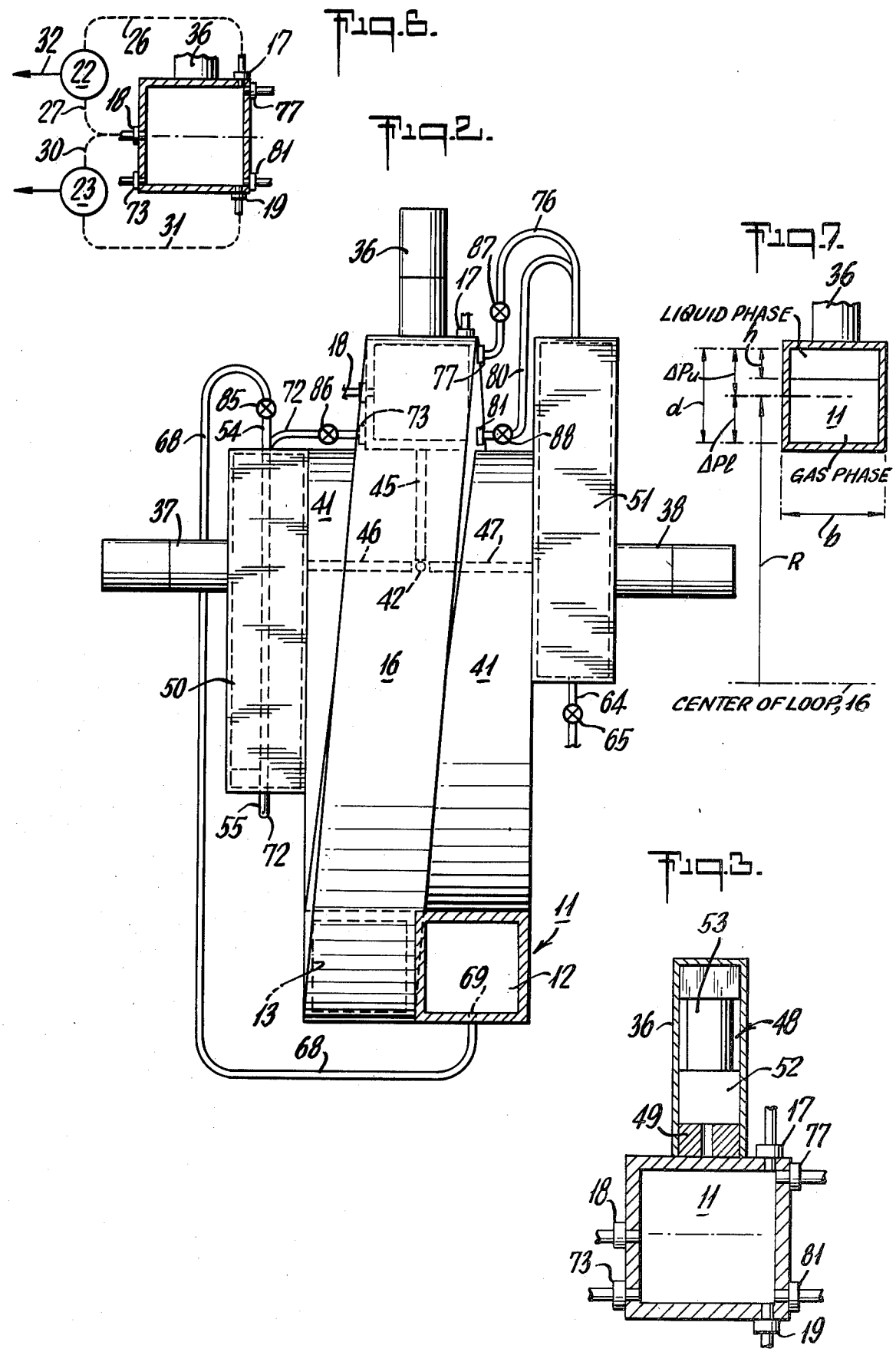

MULTIPHASE FLUID FLOW METER (D#76,244)

BACKGROUND OF THE INVENTION

1. Field of the Invention

This invention concerns a fluid flow meter in general. More specifically, it relates to an improved fluid flow meter that is particularly applicable to measuring a fluid having as one of its constituents a gas.

2. Description of the Prior Art

A multiphase fluid flow meter has been developed which employs centrifugal force on the flowing fluid. While that meter (which is described in U.S. Pat. No. 4,144,754, issued Mar. 20, 1979) was applicable to fluids of unknown density or to fluids having mixed phases of unknown proportions, it was unable to make accurate measurements in situations where the rate of flow of a gas constituent differed from the rate of flow of the liquid constituent or constituents of a mixture.

Consequently, it is an object of this invention to provide additional capabilities for a meter that employs centrifical flow and that measures densities of the fluid flowing therethrough.

Another object of the invention is to provide an instrument which will allow measurement of gas and liquid flow rates in a common pipe line, even though these two constituents are moving at different speeds.

SUMMARY OF THE INVENTION

Briefly, the invention relates to an improved multiphase fluid flow meter wherein one of the phases is a gas. It comprises a conduit for said fluid to flow therethrough. The conduit includes a full circle loop for subjecting said fluid to centrifugal force. It also comprises first means for measuring the pressure differential between the center and outside radii on said loop, and second means for measuring the pressure differential between the inside and center radii on said loop. It also comprises means for measuring the average density taken radially across the fluid flowing through said loop, and means for measuring the density of said gas phase, as well as means for measuring the density of the liquid phase. All of the elements are combined so that the rates of fluid flow including that of the said gas flowing through the meter, may be measured.

Again briefly, the invention concerns an improved two-phase fluid flow meter, wherein the said phases are gas and liquid. It comprises a conduit for said fluid to flow therethrough. The said conduit includes a full circle loop for subjecting said fluid to centrifugal force. It also comprises first means for measuring the pressure differential between the center and outside radii on said loop, and second means for measuring the pressure differential between the inside and center radii on said loop. It also comprises a first gamma ray densitometer for measuring the average density radially across the fluid going through said loop, and a second gamma ray densitometer for measuring the density of said gas phase. It also comprises a third gamma ray densitometer for measuring the density of said liquid phase, and first chamber means for holding a dynamically changing sample of said gas phase. It also comprises second chamber means for holding a dynamically changing sample of said liquid phase, and a common gamma ray source for said densitometers. It also comprises a first means for collimating said gamma ray source directed radially across said loop to make said average density measurement, and a second means for collimating said gamma ray source directed across said first chamber means to make said gas phase density measurement. It also comprises a third means for collimating said gamma ray source directed across said second chamber means to make said liquid phase density measurement. And, it comprises first and second siphon means connected to said first and second chamber means for continuously drawing fresh samples of said gas and liquid phases into said chamber means.

BRIEF DESCRIPTION OF THE DRAWINGS

The foregoing and other objects and benefits of the invention will be more fully set forth below in connection with the best mode contemplated by the inventors of carrying out the invention, and in connection with which there are illustrations provided in the drawings, wherein:

FIG. 2 is an end elevation of the meter illustrated in FIG. 1;

FIG. 3 is a somewhat enlarged fragmentary cross-sectional view taken along the lines 3—3 of FIG. 1 and looking in the direction of the arrows;

FIG. 6 is a schematic diagram illustrating the connections that are employed in making pressure differential measurements from the center to the top and bottom of the loop; and FIG. 7 is a schematic diagram which is useful in some of the theoretical explanations.

DESCRIPTION OF THE PREFERRED EMBODIMENT

Figure 1:
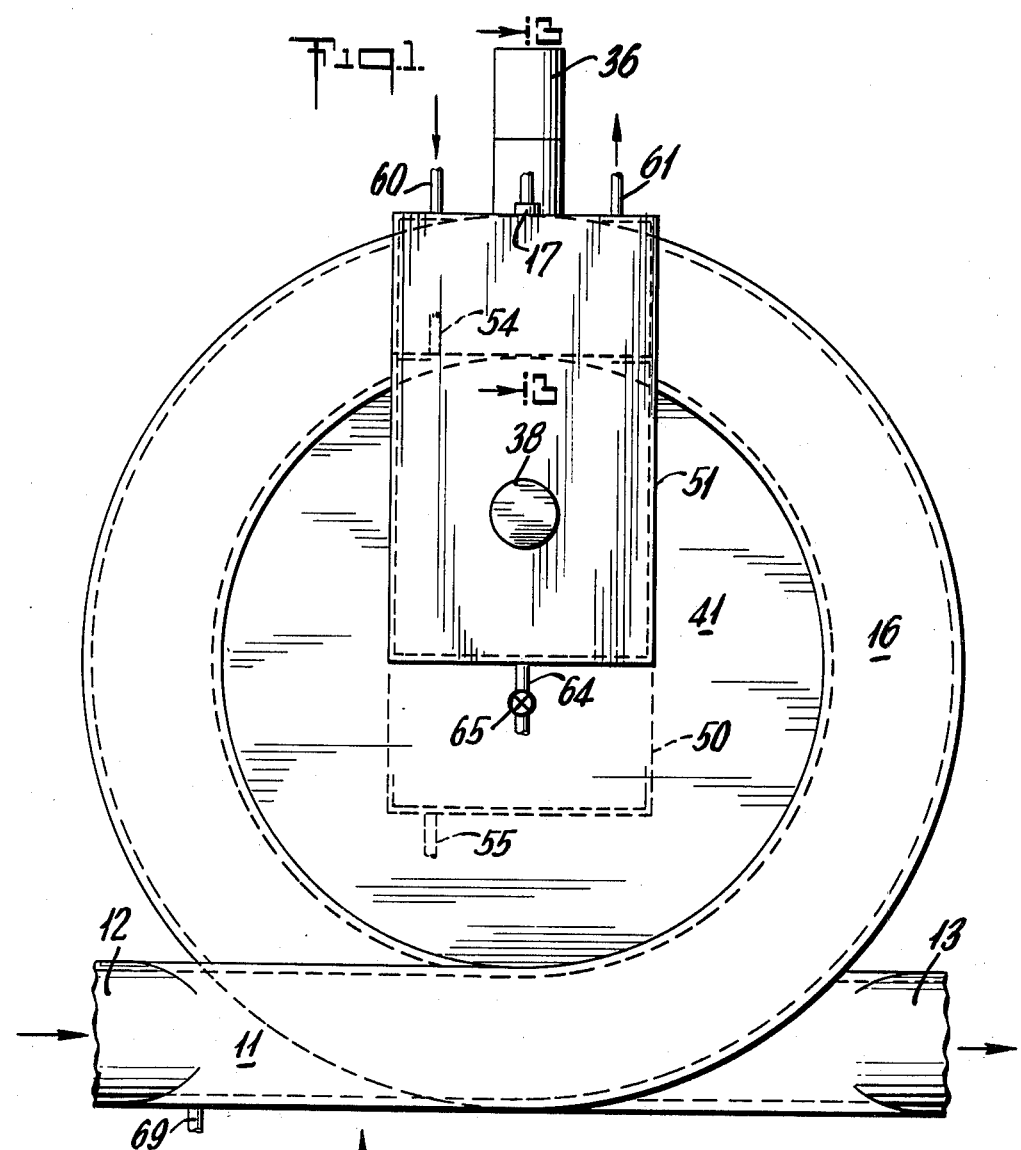
FIG. 1 is a schematic side elevation, illustrating the elements of a meter according to the invention.

As indicated in the above mentioned U.S. Pat. No. 4,144,754, the petroleum industry has many applications for multiphase flow meters. This invention provides for improving a meter according to that patent so that the fluid flow measurement may include conditions where the rate of flow of a gas constitutent is different from the rate of flow of the liquid portion.

The figures of drawing illustrate a meter according to this invention. It will be observed that the meter includes a conduit 11 for carrying the fluid through the meter, it has an inlet 12 and an outlet 13. The conduit 11 includes a full circle loop 16 that connects the inlet 12 with the outlet 13. It subjects the fluid flowing through the conduit 11 to centrifugal force.

At the top of the loop 16, there are three pressure taps 17, 18 and 19 that are illustrated most clearly in FIGS. 3 and 6. These are employed for measuring the pressure differential between the center of the loop (tap 18) and the inside and outside (taps 19 and 17 respectively) measured radially of the loop circle.

The foregoing pressure differential measurements may be carried out as indicated by FIG. 6, where there is shown schematically the connections for carrying the pressure from taps 17, 18 and 19 to each of a pair of pressure-differential instruments 22 and 23, respectively. These may be like an instrument manufactured by Rosemount Inc. of Minneapolis, Minn. which is designated as its model 1151 DP differential pressure transmitter.

The pressure at the tap 17 is transmitted via a connection 26 (dashed line) to the pressure differential instrument 22. The tap 18 is also connected to the instrument 22 via another pressure connection 27, also indicated by a dashed line.

Similarly, the pressure differential between the center radius (where tap 18 is located) and the inside radius (where tap 19 is located) is measured by the other pressure differential instrument 23. It has fluid pressure connections as indicated by dashed lines 30 and 31. The instruments 22 and 23 may have electrical output signals which are carried over circuit connections 32 and 33, indicated.

The flow meter illustrated includes a first gamma ray densitometer 36 which measures the average density taken radially across the fluid flowing within the loop 16 at the top of the loop. There is a second densitometer 37 that measures the density of the gas phase only of the fluid flowing through the meter. In addition, there is a third densitometer 38 that measures the density of the liquid phase. The flow meter includes a short cylindrical block 41 of heavy metal, e.g., lead. The block 41 is located inside of the loop 16, and centrally located inside the upper portion of the block 41, there is a gamma ray source 42 (FIG. 2). It may be 1.3 millicuries of cesium 137. The radiation from the source 42 is collimated by three passages 45, 46 and 47 that are indicated by dashed lines in FIG. 2.

Each of the densitometers 36, 37 and 38 are made up of a scintillation detector 48 (see FIG. 3) which has the input collimated by a lead sheath 49 that is incorporated in each instrument. Such column is, of course, in alignment with each of the collimating passages 45, 46 and 47, respectively.

It will be observed that the location of densitometer 36 is such that the radiation path 45 goes directly across the interior of the loop 16 at the top thereof. And, in the case of the densitometers 37 and 38, the collimating passages 46 and 47 direct rays from the source 42 across the interior of each of a dynamic sample containing chamber 50 and 51 respectively.

Each densitometer 36, 37 and 38 includes as part thereof a crystal 52 which is coupled to a photomultiplier tube 53 all of these within the detector portion of the densitometers. A detector of this type may be one like that manufactured by Bycron Corp. of Newberry, Ohio, which is designated as a scintillation detector. It will be understood that the crystal may be a sodium iodide crystal doped with thallium. And, in its use with this invention, it will be biased to count only primary (unscattered) gamma radiation that is emitted by the source 42. Such primary gamma radiation is determined by the count rate of the detector in each of the densitometers 36–38, and this count rate will have a direct relationship to the density of the fluids in the path of the collimated gamma rays in each case.

Figure 5:
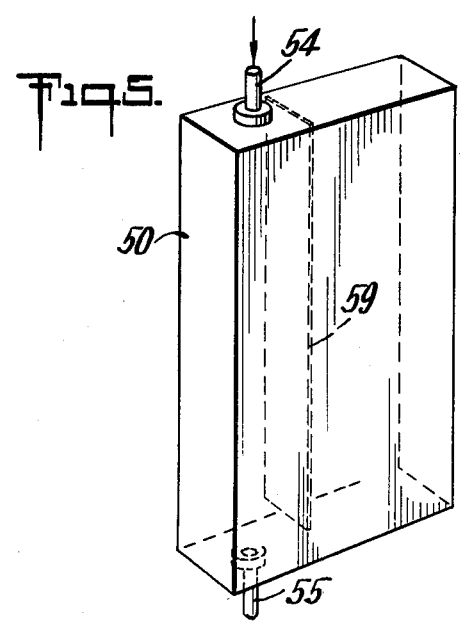
FIG. 5 is a perspective view of the gas sample containing chamber.

The gas sample chamber 50 is shown individually in FIG. 5. It will be noted that there is an inlet conduit connector 54 at the top and an outlet connector 55 at the bottom. Also, it will be noted that there is an interior barrier or partition 59 in the chamber 50. It is impervious to both the gas and liquid constituents of the fluid, and it extends from the top and joins both sides down close to the bottom but leaving a passageway underneath inside the chamber.

Figure 4:
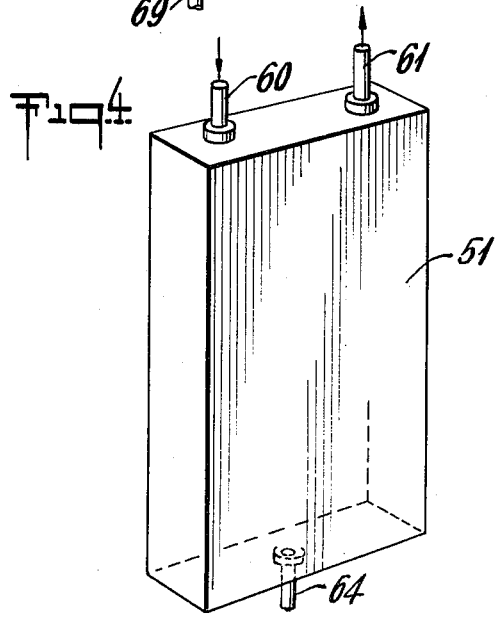
FIG. 4 is a perspective view of the liquid-sample containing chamber.

The other sample chamber 51 is illustrated individually in FIG. 4. It has an inlet connector 60 at the top of the chamber near one side, and an outlet connector 61 at the top of the connector near the other side. There is also a drain connector 64 at the bottom which has a valve 65 included. The latter is ordinarily maintained closed.

There are siphon means connected to each of the dynamic sample chambers 50 and 51. These constitute conduits, or tubes that are connected as indicated in FIG. 2. Thus, the gas sample chamber 50 has its inlet connector 54 connected via a pipe 68 that connects with a tap or connector 69 at the bottom of the conduit 11 near the inlet 12 thereof. The outlet connector 55 is connected via a pipe 72 to a tap 73 (FIG. 3) that is located on one side at the bottom of the conduit 11, near the top of the loop 16.

The liquid sample chamber 51 has its inlet connector 60 connected by a pipe 76 to a tap 77 that connects to the interior of the conduit 11 at the other side from tap 73 and at the top of the conduit, near the top of the loop 16, as clearly indicated in FIG. 3. The outlet connector 61 is connected via a pipe 80 to a tap 81 that connects into the conduit 11 near the bottom where the pressure is reduced by the centrifugal action of the fluid flowing therein.

It may be noted that there are valves 85, 86, 87 and 88 that are located in the pipes 68, 72, 76 and 80 respectively of the siphon connections just described. These values are ordinarily maintained open when the system is in operation.

It will be understood that the dynamic action of the sampling chambers causes continuously renewed samples of the gas and liquid phases to take place because of the siphoning action that is caused by the piping connections described above. Thus, in the case of the gas sample, there is the connection at tap 69 which draws off fluid near the inlet 12 of the conduit 11 of the flow meter. This sample of the fluid then goes into the chamber 50 via the inlet connector 54 at the top to one side. The fluid is directed into the chamber on the one side of the partition 59, and the liquid constituent tends to flow out through the outlet connector 55, while the gas constituent tends to separate out and rise into and fill the chamber 50 on the other side of the partition 59. Thus, the liquid portion of the fluid being drawn into the chamber 50 is carried away through the pipe 72 into the low pressure side of the conduit 11 at the top of the loop 16, via the tap 73. This action maintains a continuously changing sample of the gas constituent of the fluid flowing through the meter. In the chamber 50, the gas sample is retained where the densitometer 37 can measure it.

In chamber 51, the liquid constituent sample goes into the chamber with a continuous change that is caused by the inlet conductor 60 being connected via its pipe 76 to the tap 77 located on one side near the top of the conduit 11 and at the top of the loop 16. Here the pressure is higher because of the centrifugal action on the fluid flowing through the meter. The sample fluid (largely liquid) settles in the chamber 51. But, it is continuously withdrawn through the outlet connector 61 and the pipe 80 which leads back to the tap 81 where it rejoins the fluid flowing through the meter at the low pressure (largely gas) portion of the stream.

With reference to FIG. 7, it will be understood that centrifugal force acting upon the fluid as it passes through the loop 16 tends to separate the liquid phase from the gas phase. The commonly heavier liquid phase forms a layer of a thickness "h" on the outside wall of conduit 11 whereas the gaseous phase moves toward the inside wall of the conduit, as shown in FIG. 7. Densitometer 36 measures the average density $\bar{\rho}$ radially across the flowing fluid. Combining the densities $\rho_L$ of the liquid phase and $\rho_G$ of the gaseous phase as determined by densitometers 38 and 37 respectively with the average density $\bar{\rho}$ the thickness h of the liquid layer can be calculated according to equation $$h = (\bar{\rho} - \rho_G / \rho_L - \rho_G) d \qquad (1)$$

where d is the linear inside dimension. The general theory developed by Cortelyou and published by J. P. Cortelyou in an article entitled "Centrifugal Flow Measurement", (published in Instruments and Control System, Vol 3, February 1960, pp. 276-280) provides the basis for the expressions which relate the differential pressures $\Delta P_u$ and $\Delta P_l$ measured across the pressure tap pairs 17–18 and 18–19 (FIG. 3) to the volume flow rate of the liquid phase and to the volume flow rate of the gaseous phase.

The volume rate of the liquid phase $Q_L$ and of the gaseous phase $Q_G$ are given by the equations $$Q_L = b h \left[ R + \frac{d-h}{2} \right] f_L \qquad (2)$$

and $$Q_G = b [d-h] \left[ R - \frac{h}{2} \right] f_G \qquad (3)$$

where b and d are the linear inside dimensions of conduit 11, R is the radius of loop 16, and h is the thickness of the liquid phase as determined by equation (1). $f_L$ and $f_G$ are the angular velocities with which liquid and gas, respectively, pass through conduit 11. The angular velocities can be calculated from the pressure differentials $\Delta P_u$ and $\Delta P_l$, conduit and loop dimensions, layer thickness h and the densities $\rho_L$ and $\rho_G$, of liquid and gas, respectively, according to the following equations and conditions.

If h is calculated from equation (1) to be equal or less than d/2, that is the liquid/gas interface is within the upper half of conduit 11, the following equations (4) and (5) must be used to calculate $f_L$ and $f_G$.

$$f_L = \sqrt{[\Delta P_u K_G - P_l K_{Gu}] / [K_{Lu} K_{Gl}]} \qquad (4)$$

$$f_G = \sqrt{\Delta P_l / K_{Gl}} \qquad (5)$$

where $$K_{Lu} = \frac{1}{g} \left[ \rho_L h \left( R + \frac{d-h}{2} \right) \right]$$

$$K_{Gu} = \frac{1}{4g} \left[ \rho_G (d - 2h) \left( 2R + \frac{d-2h}{2} \right) \right]$$

$$K_{Gl} = \frac{1}{2g} \left[ \rho_G d \left( R - \frac{d}{4} \right) \right]$$

g = gravitation constant

If h is calculated from equation (1) to be larger than d/2, that is the liquid/gas interface is within the lower half of conduit 11, the following equations (6) and (7) must be used to calculate $f_L$ and $f_G$.

$$f_L = \sqrt{\Delta P_u / M_{Lu}} \qquad (6)$$

$$f_G = \sqrt{[\Delta P_l M_{Lu} - \Delta P_u M_{Ll}] / [M_{Lu} - M_{Gl}]} \qquad (7)$$

where $M_{Lu} = \frac{1}{2g} \left[ \rho_L d \left( R + \frac{d}{4} \right) \right]$ $$M_{Ll} = \frac{1}{4g} \left[ \rho_L (2h - d) \left[ 2R - \left( \frac{2h-d}{2} \right) \right] \right]$$

$$M_{Gl} = \frac{1}{g} \left[ \rho_G (d - h) \left( R - \frac{h}{2} \right) \right]$$

g = Gravitation constant

The terms on the right hand side of equations (4), (5), (6) and (7) are either known or determined from the density measurements according to equation (1) and measured differential pressures.

Equations (4) and (5) may be substituted into equations (2) and (3) which will provide the liquid phase volume rate $Q_L$ and the gaseous phase volume rate $Q_G$ if $\bar{\rho}$ is determined such that the condition $h \leq d/2$ is fulfilled.

Equations (6) and (7) may be substituted into equations (2) and (3) which will provide $Q_L$ and $Q_G$ if $\bar{\rho}$ is determined such that the condition $h > d/2$ is fulfilled.

It may be noted that an important advantage of a flow meter according to this invention, is the ability to measure rate of flow of the constituents, both gas and liquid, even where the rate of flow of the gas is different from the rate of flow of the liquid.

It will be appreciated that, in order to make the determinations, it is useful to include measurements of temperature and a temperature sensor may be included in a manner similar to that shown and described in the aforementioned U.S. patent.

While a particular embodiment of the invention has been described above in considerable detail in accordance with the applicable statutes, this is not to be taken as in any way limiting the invention, but merely as being descriptive thereof.

We claim:

1. Improved multiphase fluid flow meter wherein one of said phases is a gas, comprising
    a conduit for said fluid to flow therethrough,
    said conduit including a full circle loop for subjecting said fluid to centrifugal force,
    first means for measuring the pressure differential between the center and outside radii on said loop,
    second means for measuring the pressure differential between the inside and center radii on said loop,
    means for measuring the average density taken radially across the fluid flowing through said loop,
    means for measuring the density of said gas phase, and
    means for measuring the density of said liquid phase, all whereby rates of fluid flow including said gas flowing through said meter may be measured.
2. The invention according to claim 1, wherein said means for measuring the average density and for measuring the density of said gas and liquid phases each comprise a gamma ray densitometer.
3. The invention according to claim 2, wherein said means for measuring the density of said gas and liquid phases further comprise chamber means for holding samples of said gas and liquid phases.
4. The invention according to claim 3, wherein said means for measuring the density of said gas and liquid also comprise means for dynamically changing said samples held in said chamber means.

5. The invention according to claim 4, wherein said gamma ray densitometers all have a common gamma ray source, and
each of said densitometers has means for collimating said source,
one of said collimators being directed radially across said loop,
the other collimators being directed across each of said chamber means respectively to make said gas and liquid measurements.

6. The invention according to claim 5, wherein said means for dynamically changing said samples comprise siphon means connected to said chamber means for continuously drawing fresh samples of said gas and liquid phases.

7. Improved two phase fluid flow meter wherein said phases are gas and liquid, comprising
a conduit for said fluid to flow therethrough,
said conduit including a full circle loop for subjecting said fluid to centrifugal force,
first means for measuring the pressure differential between the center and outside radii on said loop,
second means for measuring the pressure differential between the inside and center radii on said loop,
a first gamma ray densitometer for measuring the average density radially across the fluid flowing through said loop,
a second gamma ray densitometer for measuring the density of said gas phase,
a third gamma ray densitometer for measuring the density of said liquid phase,
first chamber means for holding a dynamically changing sample of said gas phase,
second chamber means for holding a dynamically changing sample of said liquid phase,
a common gamma ray source for said densitometers,
a first means for collimating said gamma ray source directed radially across said loop to make said average density measurement,
a second means for collimating said gamma ray source directed across said first chamber means to make said gas phase density measurement,
a third means for collimating said gamma ray source directed across said second chamber means to make said liquid phase density measurement, and
first and second siphon means connected to said first and second chamber means for continuously drawing fresh samples of said gas and liquid phases.

8. Improved flow meter according to claim 7, wherein
said first chamber means has a capped-off portion,
said first siphon means comprises conduit means for connecting to said fluid upstream of said loop and to said loop at the inside radius thereof,
said second chamber means has an inlet and an outlet at the top thereof, and
said second siphon means comprises conduit means for connecting said inlet and outlet to said loop at the outside and inside radii thereof.

* * * * *